US00PP29979P2

(12) United States Plant Patent
Klemm et al.

(10) Patent No.: US PP29,979 P2
(45) Date of Patent: Dec. 11, 2018

(54) ***OSTEOSPERMUM* PLANT NAMED 'KLEOE16286'**

(50) Latin Name: *Osteospermum ecklonis*
Varietal Denomination: KLEOE16286

(71) Applicant: Klemm+Sohn GmbH & Co. KG, Stuttgart (DE)

(72) Inventors: Nils Klemm, Stuttgart (DE); Maike Boxriker, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,363

(22) Filed: May 31, 2017

(51) Int. Cl.
*A01H 5/02* (2018.01)

(52) U.S. Cl.
USPC ..... Plt./360

(58) Field of Classification Search
USPC ..... Plt./360, 427
CPC . A01H 5/025; A01H 5/02; A01H 5/00; A01H 6/14
See application file for complete search history.

*Primary Examiner* — June Hwu
(74) *Attorney, Agent, or Firm* — Barbara Campbell; Cochran Freund & Young LLC

(57) ABSTRACT

A new *Osteospermum* plant particularly distinguished by pink flowers and a spreading growth habit, is disclosed.

1 Drawing Sheet

Genus and species: *Osteospermum ecklonis.*
Variety denomination: 'KLEOE16286'.

BACKGROUND OF THE NEW PLANT

The present invention comprises a new and distinct variety of *Osteospermum*, botanically known as *Osteospermum ecklonis*, and hereinafter referred to by the variety name 'KLEOE16286'. 'KLEOE16286' originated from a cross-pollination conducted in the time of May to October, 2011 in Nairobi, Kenya between the proprietary female *Osteospermum* variety 'KLEOE14215' (U.S. Plant Pat. No. 26,694), and the proprietary male *Osteospermum* variety 'OE-2001-U 088' (unpatented).

The seeds from the cross were sown and plants were grown in a greenhouse for evaluation, where an individual plant designated 'KLEOE16286' was selected from the group of plants in May 2012 in Stuttgart, Germany. In September 2013 in Stuttgart, Germany, 'KLEOE16286' was first vegetatively propagated by vegetative terminal cuttings. 'KLEOE16286' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Pink flowers; and
2. A spreading habit.

DESCRIPTION OF THE PHOTOGRAPH

This new *Osteospermum* plant is illustrated by the accompanying photograph which shows the plant's overall plant habit including form, foliage, and flowers. The photograph is of an 8-week-old plant grown in a greenhouse in Stuttgart, Germany in April 2015. The colors shown are as true as can be reasonably obtained by conventional photographic procedures.

DESCRIPTION OF THE NEW VARIETY

The following detailed descriptions set forth the distinctive characteristics of 'KLEOE16286'. The data which define these characteristics were collected from asexual reproductions carried out in Latina, Italy in April 2017. Data was collected on six-month-old plant grown outdoors in March 2017. Color references are to The R.H.S. Colour Chart of The Royal Horticultural Society of London (R.H.S.), 5$^{th}$ edition (2007).

Classification:
- *Family.*—Asteraceae.
- *Botanical.—Osteospermum ecklonis.*
- *Common.—Osteospermum.*
- *Designation.*—'KLEOE16286'.

Parentage:
- *Female parent.*—The proprietary female *Osteospermum* variety 'KLEOE14215' (U.S. Plant Pat. No. 26,694).
- *Male parent.*—The proprietary male *Osteospermum* variety 'OE-2001-U 088' (unpatented).

Plant:
- *Form and habit.*—Herbaceous perennial but usually cultivated as an annual; not frost resistant.
- *Habit.*—Spreading.
- *Height (from top of soil).*—14.0 cm.
- *Width.*—42.0 cm.
- *Natural flowering season.*—Spring to autumn.
- *Propagation.*—Terminal cuttings.
- *Time to produce a finished flowering plant.*—About 7 weeks.
- *Time to initiate and develop roots.*—Between 3 and 4 weeks.
- *Root description.*—Light tan in color.

Stems:
- *Total number of branches per plant.*—5.
- *Length.*—28.0 cm.

*Diameter.*—0.4 cm.
*Internode length.*—1.6 cm.
*Color.*—RHS 144A.
*Texture.*—Smooth, but with fine hairs.
*Stem form.*—Round.
*Anthocyanin.*—Absent.

Leaves:
*Arrangement.*—Alternate.
*Length.*—4.3 cm.
*Width.*—2.7 cm.
*Shape.*—Oblanceolate.
*Apex.*—Acute.
*Base.*—Acute.
*Margin.*—Entire.
*Texture.*—Upper surface: Leathery and smooth. Lower surface: Leathery and smooth, but covered with fine hairs.
*Immature color.*—Upper surface: RHS N137A. Lower surface: RHS 137B.
*Mature color.*—Upper surface: RHS N137A. Lower surface: RHS 137B.
*Petioles.*—Absent.
*Venation pattern.*—Pinnate.
*Venation color.*—Upper surface: RHS 144A. Lower surface: RHS 144B.

Flower buds:
*Shape.*—Round-ovoid.
*Apex.*—Obtuse.
*Base.*—Acute.
*Height.*—0.9 cm.
*Width.*—0.6 cm.
*Color.*—RHS 144C.
*Pubescence.*—Present with fine hairs.

Inflorescence:
*Type.*—Single, daisy.
*Quantity of inflorescences per plant.*—Between 15 and 20.
*Lastingness of the inflorescences on the plant.*—About 2 weeks.
*Fragrance.*—Absent.
*Inflorescence diameter.*—About 6 cm.
*Inflorescence depth (cm).*—About 1 cm.
*Disc diameter (cm).*—About 1 cm.

Disc floret:
*Quantity per inflorescence.*—About 30.
*Shape.*—Tubular.
*Tube color.*—Closed: RHS 157A (outer surface at an immature state). Mature: RHS 156D (both inner and outer surface).
*Length.*—0.4 cm.
*Diameter (at apex).*—0.1 cm.
*Apex.*—Acute.
*Apex color.*—RHS 95B.
*Base.*—Acute.
*Base color.*—RHS 156D.
*Margin of corolla.*—Entire.

Ray floret:
*Quantity per inflorescence.*—19 to 20.
*Shape.*—Oblanceolate.
*Color.*—Upper surface: Young flowers are RHS N80B with a ring colored RHS 83B and weak longitudinal stripes colored RHS 77D and a white margin of RHS NN155D; main color fades to RHS N80C with stripes fading to RHS N78C. Lower surface: RHS N81A with stripes of RHS 10B; main color fades to RHS 83D and stripes fade to RHS 12C.
*Length.*—3.0 cm.
*Width.*—1.0 cm.
*Apex.*—Rounded.
*Base.*—Acute.
*Margin.*—Entire.
*Texture.*—Upper surface: Smooth. Lower surface: Smooth, shiny.

Peduncle:
*Length.*—8.9 cm.
*Diameter.*—0.15 cm.
*Texture.*—Smooth.
*Color.*—RHS 143C.
*Strength.*—Medium.

Phyllaries:
*Observed quantity per plant.*—15.
*Shape.*—Lanceolate.
*Arrangement.*—Single.
*Apex.*—Acute.
*Base.*—Obtuse.
*Margin.*—Entire with fine hairs.
*Length.*—1.0 cm.
*Width.*—0.15 cm.
*Texture.*—Upper surface: Smooth with fine hairs. Lower surface: Smooth.
*Color.*—Upper surface: RHS 143A. Lower surface: RHS 143B.

Reproductive organs:
*Androecium.*—Location: On the disc floret. Stamens: Quantity: About 50. Shape: Filamentous. Filament length: 0.9 cm. Filament color: RHS 155C. Anther: Shape: Lanceolate. Color: RHS 155C. Length: 0.1 cm. Pollen: Color: RHS 15A. Amount: Sparse.
*Gynoecium.*—Location: On the base of the ray florets. Pistils: Number: About 20, one per ray floret. Length: 0.4 cm. Diameter: Less than 0.05 cm. Stigma: Color: RHS 79A. Shape: Tapering filamentous and split in two parts. Length: 0.2 cm. Diameter: Less than 0.05 cm. Style: Color: RHS 79A. Length: 0.4 cm. Diameter: Less than 0.05 cm. Ovary: Arrangement: Upright. Color: RHS 145D. Diameter: 0.1 cm. Length: 0.3 cm.

Fruit and seed set: None observed.

Disease and pest/insect resistance: No disease and pest/insect resistance observed.

COMPARISON WITH PARENTAL LINES AND KNOWN VARIETY

'KLEOE16286' is a distinct variety of *Osteospermum* and is distinguished from its parents as described in Table 1.

TABLE 1

Comparison with Parental Lines

| Characteristic | 'KLEOE16286' | Female Parent 'KLEOE14215' | Male Parent 'OE-2001-U 088' |
|---|---|---|---|
| Habit | Spreading | Spreading | Upright |
| Ray floret color | Pink | White | Pink |

'KLEOE16286' is most similar to the commercial *Osteospermum* variety 'KLEOE12197' (unpatented). Differences between the varieties are described in Table 2.

TABLE 2

| Comparison with Similar Variety | | |
|---|---|---|
| Characteristic | 'KLEOE16286' | 'KLEOE12197' |
| Habit | Spreading | Upright |

We claim:

1. A new and distinct variety of *Osteospermum* plant designated 'KLEOE16286' as illustrated and described herein.

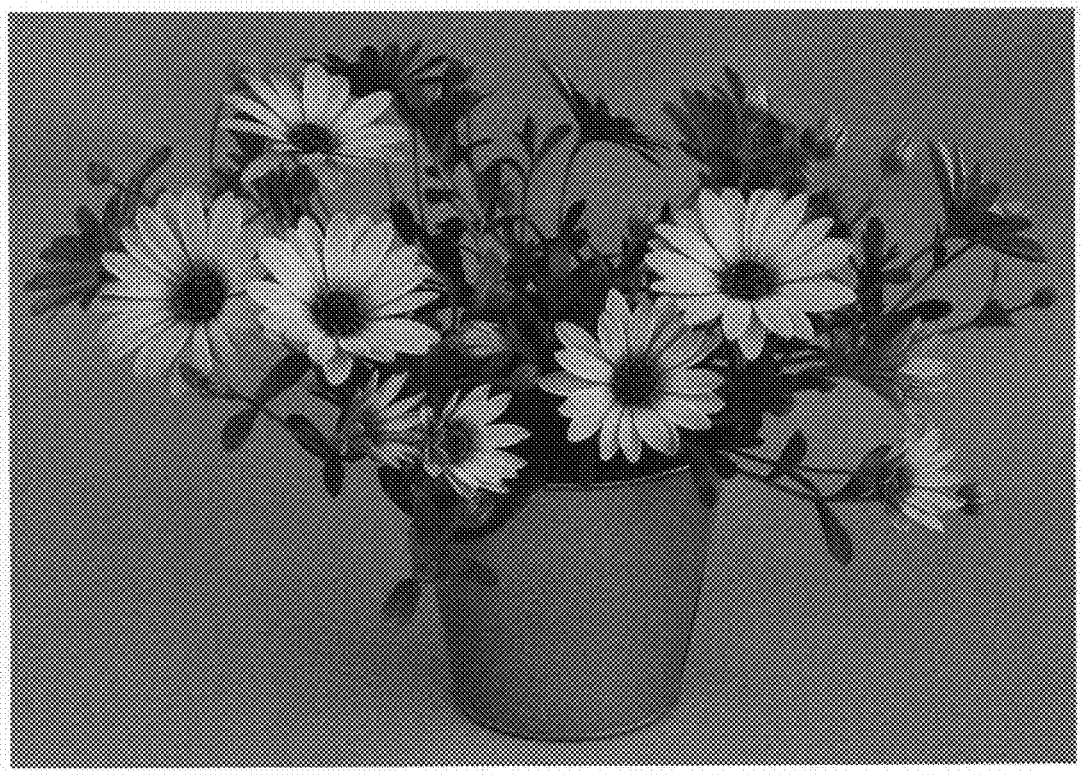

* * * * *